United States Patent [19]

Fukushima et al.

[11] Patent Number: 5,175,005
[45] Date of Patent: Dec. 29, 1992

[54] METHOD OF CONTROLLING LUNG TUMOR CELL METASTASIS

[75] Inventors: Koji Fukushima, Tama; Tsutomu Honjo, Yokohama; Tomonobu Fujita, Tokyo; Haruhisa Fujita, Yokohama; Toshiharu Sakurai, Kawasaki, all of Japan

[73] Assignee: Morinaga & Co., Ltd., Tokyo, Japan

[21] Appl. No.: 416,066

[22] Filed: Oct. 2, 1989

[30] Foreign Application Priority Data

May 19, 1989 [JP] Japan ................. 1-126387

[51] Int. Cl.⁵ ............................. A61K 35/50
[52] U.S. Cl. ........................ 424/583; 514/2; 514/21; 530/327; 530/328; 530/350; 530/851
[58] Field of Search ............ 424/583; 574/2, 21; 530/327, 328, 350, 851

[56] References Cited

U.S. PATENT DOCUMENTS

| | | | |
|---|---|---|---|
| 4,552,888 | 11/1985 | Koppel et al. | 514/474 |
| 4,599,331 | 7/1986 | Schreiber et al. | 514/179 |
| 4,966,964 | 10/1990 | Shapiro et al. | 530/316 |
| 5,019,556 | 5/1991 | Shapiro et al. | 424/583 |

FOREIGN PATENT DOCUMENTS 0291686 11/1988 European Pat. Off. .

OTHER PUBLICATIONS

"Summary of Results and General Correlations", *Cancer Res. Supp.*, 3, 1-13 (1955).
Geraldi et al., "Selectivity of the Antimetastatic and Cytotoxic Effects of 1-p-3, 3-Dimethyl-1-triazeneno)-benzoic Acid Potassium Salt, (±)-1,2-Di(3,5-dioxopiperazin-1-yl)propane, and Cyclophosphamide in Mice Bearing Lewis Lung Carcinoma," *Cancer Research*, 41, 2524-1548 (1981).
Goldin et al., "Current Results of the Screening Progran at the Division of Cancer Treatment," National Cancer Institute, Europ J. Cancer, vol. 17, pp. 129-142.
Frank S. Lee et al., Primary Structure of Human Placental Ribonuclease Inhibitor, Biochemistry 1988, 27, pp. 8545-8553.
Shapiro et al., "Human placental ribonuclease inhibitor abolishes both angiogenic and ribonucleolytic activities of angiogenin", Apr. 1987, pp. 2238-2241, Proc. Natl. Acad. Sci. vol. 84.
Chemical Abstracts, vol. 109, No. 21, Nov. 21, 1988, p. 282, Abstract 109:185714.

*Primary Examiner*—Douglas W. Robinson
*Assistant Examiner*—Jean C. Witz
*Attorney, Agent, or Firm*—Frishauf, Holtz, Goodman & Woodward

[57] ABSTRACT

A method of controlling tumor cell metastasis comprising administering to a human a therapeutically effective amount of a ribonuclease inhibitor.

7 Claims, 1 Drawing Sheet

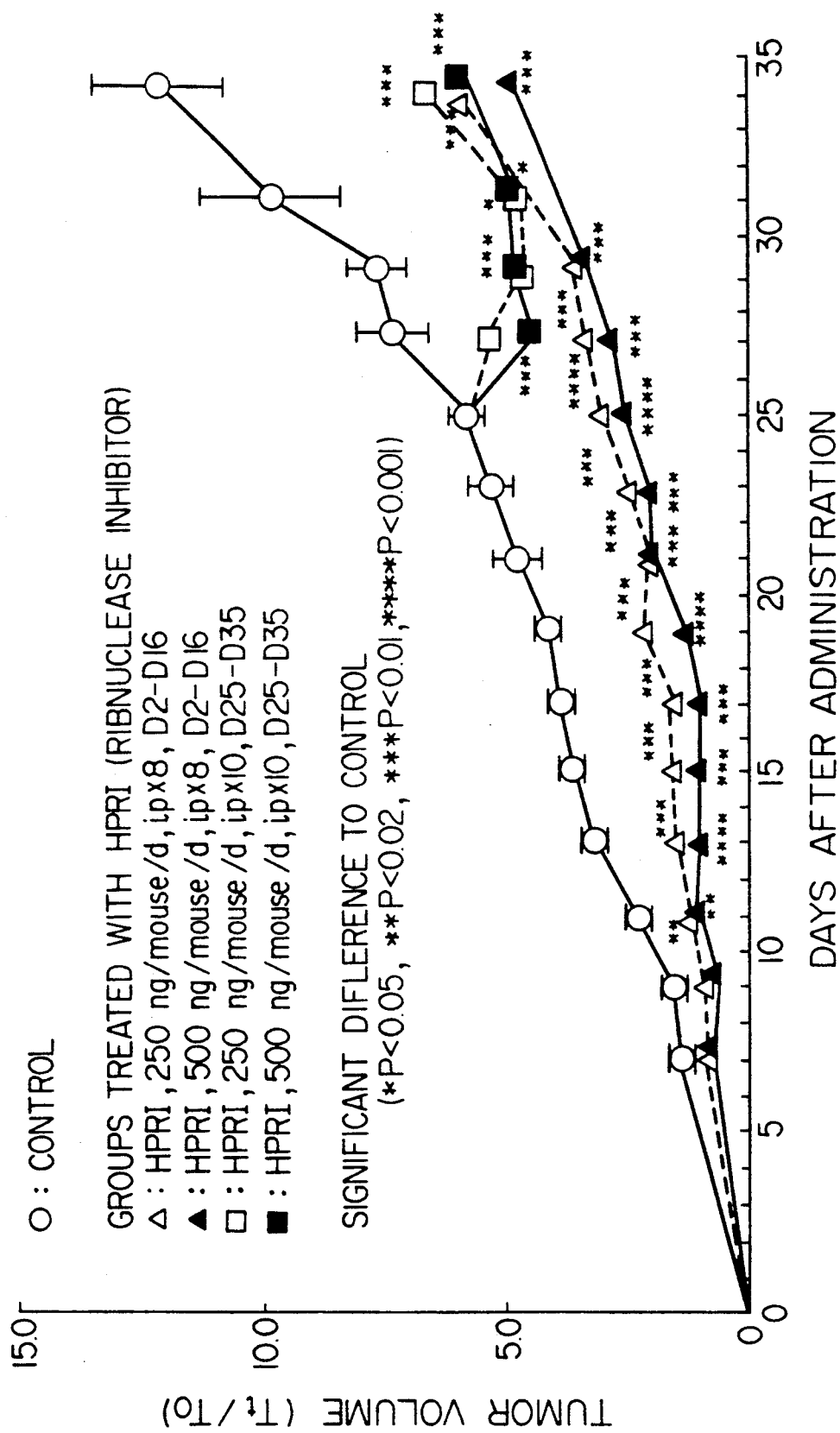

METHOD OF CONTROLLING LUNG TUMOR CELL METASTASIS

FIELD OF THE INVENTION

The present invention relates to an antitumor or antineoplastic agent and a tumor cell metastasis suppressive agent (hereinafter "antimetastatic agent"). Stated more specifically, it relates to an antitumor agent having a ribonuclease inhibitor as an active component, and more particularly to an antitumor agent capable of showing a remarkable effect on solid tumors. It further relates to an antimetastatic agent that can promise a suppressive effect against tumor cell metastasis occurring from primary nests such as lung, breast and colon cancers, in particular, against metastasis of lung tumor cells to the lungs.

BACKGROUND OF THE INVENTION

At present, methods for the cancer therapy include surgical therapy (surgery), radiotherapy, chemotherapy, and immunotherapy. Of these, surgery and radiotherapy are meaningful as most of the eradicative therapeutics. Since, however, surgery and radiotherapy are both local treatments, these treatments are useful so long as tumors are limited in a local region, but there is a serious limit when tumors are of progressive nature to spread out of the local region or diseases are systematic. On the other hand, chemotherapy and immunotherapy have the characteristic of systemic treatments. Both belong to therapeutics of a relatively new field, but they are making remarkable progress that they can be included in a territory that can expect the further development in future.

Surgery, radiotherapy and immuno-chemotherapy are treatments having different principles from each other, and hence have effects and limitations which are different on their own accord. Thus, an appropriate combination of these various treatments can be useful for enhancing remedial effects as a result of mutual cooperative action and mutual compensation for what are not enough. Such many-sided intensive composite therapeutics could for the first time bring about an improvement in the treatment of malignant tumors. With respect to composite therapeutics, a matter requiring immediate attention is to establish the therapeutics based on a new viewpoint of suppressing the neovascularization of tumor cells.

Conventional chemotherapy of cancer has been prevailingly carried out using multiple-agent combination therapeutics in which an inhibitory agent to the synthesis of nucleic acid or protein, as typified by 5-fluorouracil (5-FU), mitomycin (MMC), cisplatin (CDDP) or adriamycin (ADR), is mainly used. These, however, have so strong a side effect that the chemotherapy is restricted to the territory of an auxiliary treatment and also their use is very limited in quantity taking account of the side effect. Thus, under the existing conditions, no satisfactory therapeutic results can be obtained.

In recent years, on the other hand, an attempt has been made to treat cancer by enhancing a foreign body exclusion mechanism which is an immunological defensive mechanism inherently possessed by organisms. Typical medicaments used for that purpose are known to include various lymphokines including interferons and interleukins. By nature, however, these substances are all locally produced only when a foreign body has invaded an organism, to locally cause various biological responses, so that it has often occurred that side effects such as thermacogenesis appears as a result of general administration of these substances for the purpose of their application to the treatment of cancer. Moreover, probably because cancer cells are recognized as foreign bodies by organisms with difficulty, the cancer to which the treatment can be applied is very limited. Thus, under existing conditions, the therapeutic results cannot be said to be so good.

As discussed in the above, the antitumor agents comprising the inhibitory agent to the synthesis of nucleic acid or protein, conventionally used in clinical fields, have a strong side effect and are not in a satisfactory state also from the viewpoint of the effect.

Antitumor agents utilizing immunopotentiation action to organisms, what are called biological response modifier (BRM) preparations, also have side effects such as thermacogenesis and moreover have required great limitations on the type of the tumors to be treated.

SUMMARY OF THE INVENTION

An object of the present invention is to provide an antitumor agent and an antimetastatic agent that employs a substance having a low toxicity, originating from organism components, to enable the treatment of cancer that utilizes the control mechanism inherent in organisms.

To achieve the above object, the present invention provides an antitumor agent and an antimetastatic agent having a ribonuclease inhibitor as an active component, which is a substance particularly effective as an antitumor agent for the treatment of lymphocytic leukemia, brain tumor, cancer of the lungs, cancer of the breast, cancer of the liver, cancer of the stomach, and cancer of the large intestine, as well as melanoma cells and so forth, or a substance effective as an antimetastatic agent against the metastasis to the lungs and metastasis to the lymph nodes.

The substance of the present invention has a high antitumor activity, and shows a remarkable effect to solid cancer such as cancer of the breast and cancer of the colon. It is also effective against the metastasis to the lungs and metastasis to the lymph nodes which are questioned when the solid cancer in these primary nests has been surgically delivered, so that it can well cope with the defense of metastasis after operation. Moreover, because of a very low toxicity, it also has the characteristic of being usable for a long period of time. In addition, because of its water-soluble nature, it is very easy to handle, and also can give a very stable preparation.

BRIEF DESCRIPTION OF THE DRAWING

FIG. 1 is a graph to show antitumor activities of ribonuclease inhibitors against the multiplication of human colon tumor cells (Co-4) transplanted to nude mice.

DESCRIPTION OF THE PREFERRED EMBODIMENTS

The ribonuclease inhibitor is a substance capable of forming a complex together with an RNA incision enzyme, i.e., ribonuclease to specifically inhibit its activity. It is regarded as a substance that fundamentally exists in all organs and tissues of organisms, and participates in the synthesis of protein of organisms, thus deeply concerning the multiplication control of cells. At present, the ribonuclease inhibitor is used in the field of genetic engineering as a reagent that prevents a messenger RNA from being decomposed by ribonuclease, when the messenger RNA is collected from a cell.

The ribonuclease inhibitor is presumed to have a rapid multiplication ability as tumor cells have, but, different from tumor cells, and are contained in a large quantity in a highly controlled tissue As materials for preparing it, human placentas are preferably used. More specifically, the ribonuclease inhibitor can be purified from a human placenta by affinity chromatography using ribonuclease Sepharose, according to the Blackburn's method (J. Biol. Chem., Vol. 252, pp.5904–5910, 1977). The ribonuclease inhibitor is also commercially available as, for example, RNasin (Promega Biotec Co, U.S.A.), Human placental ribonuclease inhibitor (Amersham Co.. The Great Britain) and Ribonuclease inhibitor (Takara Shuzo K.K.), and thus readily available.

The ribonuclease inhibitor is a substance whose primary structure has been determined by the group of the present inventors and the group of Vellee et al, although its N terminal structure is not completely identified (Biochemistry, Vol 27, pp.8545–8553, 1988).

In the present invention, this ribonuclease inhibitor is used as the antitumor agent and antimetastatic agent, and the form of administration may be any of intravenous administration, subcutaneous administration, intramuscular administration, and intratumorous administration. As a carrier for the administration of the ribonuclease inhibitor, suited is, for example, a sterilized sodium phosphate buffered saline solution containing glutathione of a 10 mM reduced type.

There are no particular limitation on the dose of the ribonuclease inhibitor. As will be shown in Examples described later, however, a dose of from 5 to 1,000 ng/mouse brings about effect in all examples. Thus, the effect can be exhibited with its use in a very small amount. This can be calculated into from 0.25 to 50 μg/kg as a dose per 1 kg of body weight. This dose is presumed to bring about a sufficient effect to humans.

As to the toxicity of the ribonuclease inhibitor, as will be shown in Examples described later, no decrease in body weight nor change in hair luster is seen in all examples within the range of the dose in which experiments were made on mice. Thus the ribonuclease inhibitor is confirmed to have a very low toxicity. Hence, little side effect is presumed to be caused within the range of the effective dose.

The substance according to the present invention is particularly effective as an antitumor agent for the treatment of lymphocytic leukemia, brain tumor, cancer of the lungs, cancer of the breast, cancer of the liver, cancer of the stomach, and cancer of the large intestine, as well as melanoma cells and so forth, or a substance effective as an antimetastatic agent against the metastasis to the lungs and metastasis to the lymph nodes. The substance according to the present invention can also enhance its antitumor action when used in combination with known active substances.

In the present invention, the action and mechanism have not been clarified how the ribonuclease inhibitor can exhibit the antitumor action and suppression of tumor cell metastasis. The following presumption, however, can be made.

That is to say, the ribonuclease inhibitor is a protein with a molecular weight of about 50,000 and forms a 1:1 complex with angiogenin on the other hand, Lobb et al report (in Proc. Natl. Acad. Sci., Vol. 84, p.2338, 1987) that the ribonuclease inhibitor can strongly suppress the activity of the angiogenin having a neovascularization activity, and has the possibility of simultaneously inhibiting extension of the vessels newly produced to supply nutrients to tumor cells. Hence, this ribonuclease inhibitor is presumed to have the action of inhibiting the neovascularization action ascribable to angiogenin and thereby inhibiting the ribonuclease activity, and such action is presumed to exhibit the antitumor action and suppression of tumor cell metastasis.

According to experiments made by the present inventors, the ribonuclease inhibitor had no influence on the replication of cultured mammary tumor cells and normal endothelial cells, so that the substance can also be presumed to show no direct action to the cells.

However, the effect of suppressing tumor cell multiplication and life prolongation effect are remarkably seen and some animals showed complete cure, as a result of small amount intraperitoneal administration, subcutaneous administration or intratumorous administration to cancerated animals such as mice with Meth A sarcoma cells, mammary tumor cells or melanoma cells, and humans with mammary tumor cells, colon tumor cells or lung tumor cells. It is further possible to use the substance as an antimetastatic agent which is a means for preventing tumor cell metastasis after surgical operation. Namely, in a model system of metastasis to the lungs, using Lewis lung tumor cells of a mouse, a combination of treatment using the ribonuclease inhibitor and surgical operation of a primary nest resulted in a significant suppression of the metastasis to the lungs and metastasis to the lymph nodes.

EXAMPLES

The present invention will be described below in greater detail by giving Examples.

The ribonuclease inhibitor used in the following Examples was purified from a human placenta by affinity chromatography using ribonuclease Sepharose, according to the Blackburn's method (J. Biol. Chem , Vol. 252 pp.5904–5910, 1977). In administration of the ribonuclease inhibitor, a sterilized sodium phosphate buffered saline solution containing glutathione of a 10 mM reduced form and 1 mg/ml BSA were used as a carrier.

EXAMPLE 1

Tumor multiplication suppressive effect and life prolongation effect of ribonuclease inhibitor, against mouse Meth A sarcoma cells Meth A sarcoma cells in the number of $2.0 \times 10^5$ were intradermally transplanted to female Balb/c mice (6 week old), and the ribonuclease inhibitor was intratumorously or intraperitoneally administered in a dose of 10 ng/mouse, 100 ng/mouse and 1,000 ng/mouse, continuously 7 times after 10th day up to 16th day during which the sarcoma cells reached a tumor volume of from 200 to 300 mm3, and then the changes of tumor volume and average survival days were observed. For comparison, similar experiments were made on a known carcinostatic agent 5-FU, under intraperitoneal administration in a dose of 20 mg/kg/day. Results obtained are shown in Tables 1 and 2.

As a result, there was seen tumor multiplication suppressive effect in the administration in various doses. As to an optimum dose, however, a maximum effect was obtained under conditions of intratumorous administration in a dose of 100 ng/mouse, and there was obtained a better antitumor effect than the known carcinostatic agent 5-FU (20 mg/kg/day, ip×7). Even under intratumorous administration in a dose of 10 ng/mouse, a tumor multiplication suppressive effect equal to that of 5-FU was seen, and also no toxicity was seen at all. On the other hand, regarding the life prolongation effect, a significant effect was shown only in 100 ng/mouse intratumorous administration and 1,000 ng/mouse intraperitoneal administration, when compared with the control.

In the group of 100 ng/mouse intratumorous administration, ⅛ of tested mice survived for 90 days or more with observation of complete cure of the tumors. These are significant results telling that a therapeutic effect can be obtained by the administration of ribonuclease inhibitor even to the tumors in the stage they have multiplied to a certain extent.

EXAMPLE 2

Tumor multiplication suppressive effect by administration of ribonuclease inhibitor, against mouse MM46 mammary tumor cells MM46 mammary tumor cells in the number of $5 \times 10^5$ were intradermally transplanted to female C3H/He mice, and the ribonuclease inhibitor was intratumorously or intraperitoneally administered in a dose ranging from 50 to 1,000 ng/mouse, continuously 9 times from 10th day up to 18th day after transplantation. The mice were killed on 42nd day after the transplantation of tumors, and actual tumors were delivered to measure the weight of tumors. For comparison, similar experiments were made on a known carcinostatic agent nimustine, under intraperitoneal administration in a dose of 5 mG/kG/day. Results obtained are shown in Table 3.

In the 50, 100, 500 ng/mouse intratumorous adminis-

TABLE 1

Antitumor effect of ribonuclease inhibitor against mouse Meth A sarcoma cells

| Treatment | Dose (ng/mouse) | Weight change, 18th day (g) | Average tumor volume (mm³ ± SE) (%, treated group/control) | | | | |
|---|---|---|---|---|---|---|---|
| | | | 14th day | 18th day | 21st day | 23rd day | 31st day |
| Control: | — | −1.91 | 504 ± 162 | 1176 ± 285 | 2091 ± 38 | 2662 ± 696 | 6670 ± 1195 |
| HPRI (intratumorous): | 1000 | −1.45 | 212 ± 110**** (42.1) | 660 ± 327*** (56.1) | 1296 ± 582 (62.0) | 1833 ± 738* (68.6) | 4739 ± 1662* (71.0) |
| | 100 | −1.17 | 56 ± 27**** (11.1) | 124 ± 117**** (10.5) | 471 ± 425**** (22.5) | 647 ± 507**** (24.3) | 2111 ± 1237**** (31.6) |
| | 10 | −1.46 | 183.12**** (36.3) | 538 ± 326**** (45.7) | 1067 ± 545**** (51.0) | 1399 ± 629*** (52.6) | 3015 ± 939**** (45.2) |
| HPRI (intraperitoneal): | 1000 | −1.57 | 128 ± 96**** (25.4) | 302 ± 309**** (25.7) | 595 ± 530**** (28.5) | 941 ± 754*** (35.3) | 2624 ± 1724**** (39.1) |
| 5-FU: | 20 mg/kg | −0.22*** | 223 ± 89**** (44.2) | 610 ± 89**** (51.9) | 1040 ± 45**** (49.1) | 1048 ± 382**** (40.6) | 2954 ± 656**** (44.3) |

HPRI: Ribonuclease inhibitor
Significant difference of treated groups relative to the control
*P < 0.05.
***P < 0.01.
****P < 0.001 tration of the ribonuclease inhibitor, a suppressive effect as strong as 72.9% to 88.9% as a tumor multiplication suppression rate was shown. On the other hand, a suppression rate of 80.3% was also shown in the 500 ng/mouse intraperitoneal administration. On the other

TABLE 2

Life prolongation effect of ribonuclease inhibitor against mouse Meth A sarcoma cells

| Treatment | Dose (ng/mouse) | Weight change, 18th day (g) | Survival days of individuals (day) | Average survival days (day) ± SE | Life prolongation rate (treated group/control) (%) | Complete cure number/total |
|---|---|---|---|---|---|---|
| Control: | — | +1.91 | 31, 32, 32, 33, 33, 34, 35, 35, 36, 36 | 33.7 ± 0.6 | — | 0/10 |
| HPRI (intratumorous): | 1000 | +1.45 | 31, 31, 32, 35, 38, 39, 42, 44 | 36.6 ± 1.8 | 118.9 | 0/8 |
| | 100 | +1.17 | 23, 39, 42, 42, 42, 42, 52, 60 | 42.0 ± 3.9* | 136.8 | 1/8 |
| | 10 | +1.46 | 25, 30, 32, 33, 35, 37, 38, 49 | 34.9 ± 2.5 | 113.4 | 0/8 |
| HPRI (intraperitoneal): | 1000 | +1.57 | 33, 37, 42, 44, 52 | 41.6 ± 3.2* | 135.5 | 0/5 |
| 5-FU: | 20 mg/Kg | −0.22 | 24, 32, 36, 36, 37, 37, 42, 42 | 35.8 ± 2.0 | 116.4 | 0/8 |

HPRI: Ribonuclease inhibitor
Significant difference of treated groups relative to the control
*P < 0.05 hand, there was seen no significant tumor multiplication suppressive effect in nimustine (5 mg/kg/day, ip×9), from the fact of which it was confirmed that the ribonuclease inhibitor was effective in both administration routes of the intratumorous administration and intraperitoneal administration.

peritoneal administration in a dose of 5 mg/kg/day. Results obtained are shown in Tables 4 and 5.

In the 10 ng/mouse intratumorous administration of the ribonuclease inhibitor, an effect as not so strong as 35.8% as a tumor multiplication suppression rate was obtained. A suppression rate of 75% or more was

TABLE 3

Antitumor effect of ribonuclease inhibitor against mouse MM46 mammary tumor cells

| Treatment | Dose (ng/mouse) | Weight change, 20th day (g) | Tumor weight on 42nd day (mg) | Average tumor weight (mg) ± SE | Treated group/ control (%) | Complete cure number/ total |
|---|---|---|---|---|---|---|
| Control: | — | +0.40 | 3632, 3801, 3849, 5220, 7284, 7802, 8111, 8271, 10320, 10830 | 6912 ± 842 | — | 0/10 |
| HPRI (intratumorous): | 500 | +0.80 | 0, 0, 262, 383, 507, 1716, 2515, 8812# | 767 ± 365**** | 11.1 | 2/8 |
| | 100 | +1.03 | 0, 0, 0, 65, 86, 1515, 1679, 2250, 3462, 4178 | 1323 ± 496**** | 19.1 | 3/10 |
| | 50 | +0.83 | 0, 778, 1160, 1172, 1429, 1853, 1859, 4522, 4522, 10570# | 1597 ± 469**** | 27.1 | 1/10 |
| HPRI (intraperitoneal): | 1000 | −1.49 | 0, 0, 104, 1616, 1711, 3010, 4038, 7050 | 2191 ± 968*** | 31.7 | 2/8 |
| | 500 | +0.80 | 276, 276, 475, 479, 488, 1119, 1527, 1852, 5766, 10813# | 1363 ± 582**** | 19.7 | 0/10 |
| Nymstin: | 5 mg/Kg | +0.88 | 819, 827, 2929, 4131, 4515, 6088, 6452, 8673 | 4316 ± 977 | 62.4 | 0/8 |

HPRI: Ribonuclease inhibitor
Significant difference of treated groups relative to the control:
***P < 0.01
****P < 0.001
: Abandoned

EXAMPLE 3

Tumor multiplication suppressive effect and life prolongation effect by administration of ribonuclease inhibitor, against mouse MM46 mammary tumor cells MM46 mammary tumor cells in the number of $2 \times 10^5$ were subcutaneously transplanted to female C3H/He mice (6 week old), and the ribonuclease inhibitor was intraperitoneally administered in a dose ranging from 10 to 1,000 ng/mouse, continuously 9 times from 1st day up to 9th day after transplantation. The tumor volume at 14th day after the transplantation of tumors was measured, and average survival days were observed. For comparison, similar experiments were made on a known carcinostatic agent nimustine under intraperitoneal administration in a dose of 5 mg/kg/day.

shown when the intraperitoneal administration was made in doses of 50 ng/mouse, 500 ng/mouse and 1,000 ng/mouse. Like the tumor multiplication suppressive effect, a life prolongation effect of 166.8% or more as a life prolongation rate was shown in the administration in a dose of not less than 50 ng/mouse, which was superior to the effect obtained by nimustine (5 mg/kg/day, ip×9). In particular, in the group in which the ribonuclease inhibitor was intraperitoneally administered in a dose of 50 ng/mouse, 7/9 of tested mice survived for 60 days or more, and all the survived mice were completely cured animals. Hence, the mouse MM46 mammary tumor cells was also found to be a tumor cell strain having a high sensitivity to the intraperitoneal administration of the ribonuclease inhibitor.

TABLE 4

Antitumor effect of ribonuclease inhibitor against mouse MM46 mammary tumor cells

| Treatment | Dose (ng/mouse) | Weight change, 10th day (g) | Tumor volume (14th day) (mm³) | Average tumor volume (mm³) ± SE | Treated group/ control (%) | Complete cure number/ total (60th day) |
|---|---|---|---|---|---|---|
| Control: | — | +2.67 | 507, 827, 914, 945, 1146, 1464 | 967 ± 131 | — | 0/6 |
| HPRI: | 1000 | +2.16 | 0, 0, 0, 0, 0, 54, 163, 261, 389, 440, 513, 703 | 210 ± 64**** | 21.7 | 3/8 |
| | 500 | +2.22 | 0, 0, 0, 102, 175, 254, 467, 488, 614, 1118# | 233 ± 74**** | 24.1 | 3/10 |
| | 50 | +2.51 | 0, 0, 0, 69, 175, 183, 254, 286, 793# | 129 ± 42**** | 12.5 | 3/9 |
| | 10 | +2.64 | 339, 362, 5088, 609, 689, 721, 861, 888 | 622 ± 73* | 64.3 | 0/8 |
| Nymstin: | 5 mg/Kg | +0.55 | 143, 200, 345, 379, 769 | 376 ± 110* | 38.0 | 0/5 |

HPRI: Ribonuclease inhibitor
Significant difference of treated groups relative to the control:
*P < 0.05.
**P < 0.02.
****P < 0.001
: Abandoned

TABLE 5

Life prolongation effect of ribonuclease inhibitor against mouse MM46 mammary tumor cells

| Treatment | Dose (ng/mouse) | Weight change, 10th day (g) | Survival days (day) ± SE | Average survival days (day) ± SE | Life prolongation rate (treated group/control) (%) | Complete cure number/total (60th day) |
|---|---|---|---|---|---|---|
| Control: | — | −2.67 | 13, 13, 13, 13, 14, 14, 15, 15, 16, 16 | 14.2 ± 0.4 | — | 0/10 |
| HPRI: | 1000 | −2.16 | 20, 23, 31, 34, 60, 60, 60, 60, 60, 60, 60, 60, 60 | 49.8 ± 4.5**** | 350.7 | 9/13 |
| | 500 | −2.22 | 20, 25, 25, 29, 31, 31, 60, 60, 60 | 37.8 ± 5.6**** | 266.8 | 3/9 |
| | 50 | −2.51 | 34, 35, 60, 60, 60, 60, 60, 60, 60 | 54.3 ± 3.7**** | 382.6 | 7/9 |
| | 10 | −2.64 | 15, 15, 17, 23, 25, 35, 60# | 21.7 ± 3.2*** | 152.5 | 1/7 |
| Nymstin: | 5 mg/Kg | +0.55 | 25, 28, 29, 30, 35 | 29.4 ± 1.5**** | 207.0 | 0/5 |

HPRI: Ribonuclease inhibitor
Significant difference of treated groups relative to the control:
***$P < 0.01$.
****$P < 0.001$
34#: Abandoned

EXAMPLE 4

Tumor multiplication suppressive effect and life prolongation effect by administration of ribonuclease inhibitor, against mouse B16 melanoma cells Melanoma cells in the number of $1 \times 10^5$ were subcutaneously transplanted to female BDFI mice (6 week old), and the ribonuclease inhibitor was intraperitoneally administered in a dose ranging from 5 to 500 ng/mouse, continuously 20 times from 1st day up to 20th day after transplantation. The tumor volume on 21st day after the transplantation of tumors was measured, and average survival days were observed. For comparison, similar experiments were made on known carcinostatic agents cisplatin and cortisone acetate, under administration in given doses. Results obtained are shown in Tables 6 and 7.

In the administration of the ribonuclease inhibitor in a dose of from 5 to 500 ng/mouse, a tumor multiplication suppression rate of only about 50% was obtained, which did not exceed the effect of cisplatin (1 mg/kg/day, ip×20) and cortisone acetate (50 mg/kg/day, sc×20). In the administration of ribonuclease inhibitor in doses of 50 ng/mouse/day, ip×20 and 100 ng/mouse/day, ip×20, however, a significant life prolongation effect was seen though slightly inferior when compared with that of cisplatin and cortisone acetate.

TABLE 6

Antitumor effect of ribonuclease inhibitor against mouse B16 melanoma

| Treatment | Dose (ng/mouse) | Weight change, 12th day (g) | Tumor volume (21st day) (mm³) | Average tumor volume (mm³) ± SE | Treated group/control (%) |
|---|---|---|---|---|---|
| Control: | — | +2.29 | 1025, 1113, 1162, 1564, 1629, 1943, 1995, 2138, 2969, 2988 | 1853 ± 223 | — |
| HPRI: | 500 | +2.30 | 58, 133, 294, 466, 753, 843, 1175, 1532, 1831 | 786 ± 208*** | 42.4 |
| | 100 | +3.50 | 478, 749, 961, 1386, 1476 | 1233 ± 157* | 66.6 |
| | 50 | +3.83 | 29, 450, 554, 1099, 1133, 1229, 1376, 1493 | 918 ± 182*** | 49.5 |
| | 5 | +3.27 | 487, 823, 841, 943, 1020, 1403 | 916 ± 171*** | 49.4 |
| Cysplatine: | 1 mg/Kg | −0.71 | 0, 0, 159, 218, 240, 344, 459, 605, 112 | 254 ± 78**** | 13.7 |

HPRI: Ribonuclease inhibitor
Significant difference of treated groups relative to the control:
*$P < 0.05$.
**$P < 0.02$.
***$P < 0.01$.
****$P < 0.001$

TABLE 7

Life prolongation effect of ribonuclease inhibitor against mouse B16 melanoma

| Treatment | Dose (ng/mouse) | Weight change, 21st day (g) | Survival days (day) | Average survival days (day) ± SE | Life prolongation rate (treated group/control) (%) |
|---|---|---|---|---|---|
| Control: | — | +2.29 | 14#, 21, 21, 21, 21, 21, 22, 22, 22, 23 | 21.6 ± 0.2 | — |
| HPRI: | 500 | +2.30 | 21, 21, 23, 23, 24, 31, 34, 34, 41 | 28.0 ± 2.4** | 129.9 |
| | 100 | +3.50 | 28, 29, 29, 31, 32, 34, | 31.8 ± 1.0**** | 147.3 |

TABLE 7-continued

Life prolongation effect of ribonuclease inhibitor against mouse B16 melanoma

| Treat-ment | Dose (ng/mouse) | Weight change, 21st day (g) | Survival days (day) | Average survival days (day) ± SE | Life prolongation rate (treated group/control) (%) |
|---|---|---|---|---|---|
| | 50 | −3.83 | 34, 37 28, 29, 29, 31, 32, 32, 34, 38 | 31.6 ± 1.2**** | 146.7 |
| | 5 | +3.27 | 22, 22, 23, 23, 29, 34, 34, 35 | 27.8 ± 2.1*** | 128.7 |
| Cysplatine: | 1 mg/Kg | −0.71 | 20, 31, 34, 34, 36, 36, | 34.4 ± 1.8**** | 159.6 |

HPRI: Ribonuclease inhibitor
Significant difference of treated groups relative to the control
*P < 0.05.
**P < 0.02.
***P < 0.01.
****P < 0.001
: Abandoned

EXAMPLE 5

Tumor Multiplication Suppressive Effect of Ribonuclease Inhibitor According to Subrenicapsular Transplantation, against Human Colon Tumor Cells (Co-4))

A cell mass of 10 mm$^3$, of a human colon tumor cell strain was subrenicapsularly transplanted to female BDFI mice (6 week old), and the ribonuclease inhibitor was intraperitoneally administered in a dose ranging from 10 to 1,000 ng/mouse, continuously 5 times from 1st day up to 5th day after transplantation. The mice were killed on 6th day after the transplantation of tumors, and the minor axes and major axes of tumors were measured using a stereoscopic microscope to calculate the tumor volume. For comparison, similar experiments were made on known carcinostatic agents 5-FU, mitomycin C, nimustine, adriamycin and cisplatin, under administration in given doses. Results obtained are shown in Table 8.

The ribonuclease inhibitor gave an inhibitory rate ranging from about 30% to 35% in the administration in any doses, only showing a tumor multiplication suppressive effect slightly inferior to that of known carcinostatic agents. In the administration in a dose of 1,000 ng/mouse, ip×5, however, it showed an effect comparable to that of nimustine (10 mg/kg/day, ip×2).

TABLE 8

Antitumor effect of ribonuclease inhibitor against human large intestine tumor (Co-4) according to subrenicapsular method

| Treatment | Dose (ng/mouse) | Admstn. schedule | Weight change, 6th day (g) | Tumor volume ratio (size on 6th day/initial size) | Average tumor volume ratio | Treated group/control (%) |
|---|---|---|---|---|---|---|
| Control: | — | — | −0.80 | 1.500, 1.375, 1.812, 1.342 | 1.507 ± 0.107 | — |
| HPRI: | 1000 | D1-D5 | −0.97 | 0.950, 0.937, 1.000 | 0.962 ± 0.019*** | 63.8 |
| | 100 | D1-D5 | −0.33 | 1.047, 1.125, 1.083, 0.909 | 1.041 ± 0.049*** | 69.0 |
| | 10 | D1-D5 | −0.40 | 0.954, 1.105, 1.023, 1.085 | 1.041 ± 0.034*** | 69.1 |
| 5-FU: | 30 mg/Kg | D1 & D4 | 0.00 | 0.857, 0.791, 0.900, 0.833 | 0.845 ± 0.022**** | 56.0 |
| Mitomycin: | 2 mg/Kg | D1 & D4 | +0.95 | 0.857, 0.782, 0.809, 0.880 | 0.832 ± 0.022**** | 55.1 |
| Nymstin: | 10 mg/Kg | D1 & D4 | −3.8 | 0.952, 0.695, 1.117, 1.000 | 0.941 ± 0.089**** | 62.4 |
| Adriamycin: | 5 mg/Kg | D1 & D4 | −0.83 | 0.894, 0.875, 0.879, 0.900 | 0.869 ± 0.020*** | 57.6 |
| Cysplatine: | 2 mg/Kg | D1-D5 | −0.45 | 0.894, 0.789, 0.826, 0.772 | 0.820 ± 0.027**** | 54.4 |

HPRI: Ribonuclease inhibitor
Significant difference of treated groups relative to the control
***P < 0.01.
****P < 0.001

EXAMPLE 6

Antitumor activity of ribonuclease inhibitor against multiplication of human colon tumor cells (Co-4) transplanted to nude mice Co-4 tumor pieces, tumors of from 200 to 250 mm$^3$, were transplanted to female Balb/c nu/nu(−) mice, and comparative examination was made between the group in which the ribonuclease inhibitor was intraperitoneally administered 8 times at intervals of a day from 2nd day up to 16th day after the transplantation of tumors and the group in which the ribonuclease inhibitor was intraperitoneally administered every day from 25th day up to 34th day after the transplantation. Results obtained are shown in FIG. 1. The ribonuclease inhibitor was administered in a dose of 250 ng/mouse or 500 ng/mouse.

It was proved that a remarkable multiplication suppressive effect was shown in both doses in the initial administration, and the tumor multiplication suppressive effect was maintained even in the instances of the latter-stage administration started from 25th day, so long as the ribonuclease inhibitor was continued to be intraperitoneally administered. This suggests the possibility that there is any correlation between the effect of suppressing the multiplication of human colon tumor cells and the presence of ribonuclease inhibitor in organisms.

EXAMPLE 7

Antitumor Activity of Ribonuclease Inhibitor against Multiplication of Human Mammary Tumor Cells (MX 1) Transplanted to Nude Mice MX-1 tumor pieces of 2×2 mm were transplanted to female Balb/c nu/nu(−) mice, and examination was made under conditions that the time the tumor volume reached 532±139 mm$^3$ on 13th day after transplantation was assumed as 1st day and the ribonuclease inhibitor was intraperitoneally administered 6 times a week in a dose of from 5 to 500 ng/mouse/day, which administration was continued for 4 weeks Results are shown in Table 9, which were obtained by measuring tumor weights on 28th day after administration, in the groups in which the ribonuclease inhibitor was intraperitoneally administered. For comparison, similar experiments were also made on known carcinostatic agents cortisone acetate and nimustine administered in given doses. Results obtained are also shown together in Table 9.

In the group in which the ribonuclease inhibitor was intraperitoneally administered in a dose of 100 ng/mouse/day, a better antitumor effect was seen than in the groups in which cortisone acetate (50 mg/kg/day, ip×24) and nimustine (2 mg/kg/day, ip×24) were administered.

Table 10 shows typical changes in the tumor volume in the group in which the ribonuclease inhibitor was intraperitoneally administered in a dose of 100 ng/mouse/day. In this table, a tumor multiplication curve is shown as the ratio of a tumor volume ($T_o$) before administration to a tumor volume ($T_t$) after administration.

As will be evident from Table 10, the 100 ng/mouse intraperitoneal administration has brought about a remarkable tumor multiplication suppressive effect during administration, when compared with the control.

TABLE 9

| Treatment | Dose (ng/mouse) | Weight change, 28th day (g) | Tumor weight, 28th day (mg) | Average tumor weight (mg) ± SE | Treated group/control (%) |
|---|---|---|---|---|---|
| Control: | — | −7.70 | 5561, 6074, 7699, 8878, 10119, 11324, 12050, 13265 | 9371 ± 992 | — |
| HPRI: | 500 | −6.55 | 4750, 7172, 11666, 13549 | 9286 ± 2017 | 99.1 |
|  | 100 | −3.09*** | 2770, 3776, 4661, 6021, 6332, 11393# | 4714 ± 675*** | 50.3 |
|  | 25 | +7.29 | 5573, 6005, 6116, 9905, 13564 | 8233 ± 1545 | 87.8 |
|  | 5 | −5.44 | 3871, 5585, 8231, 10355, 10361, 11291 | 8299 ± 1217 | 88.6 |
| Nymstin: | 2 mg/Kg | −3.29*** | 3496, 5455, 7644, 8440, 8548 | 4783 ± 398*** | 51.0 |

HPRI: Ribonuclease inhibitor
Significant difference of treated groups relative to the control
***$P < 0.01$
Abandoned

TABLE 10

Tumor multiplication inhibitory effect of ribonuclease inhibitor against human mammary tumor cell strain (MX-1) transplanted to nude mice

| Treatment | Dose (ng/mouse) | Tumor weight ratio (volume after treatment/volume ± SE before treatment) | | | | |
|---|---|---|---|---|---|---|
|  |  | 5th day | 8th day | 10th day | 12th day | 15th day |
|  |  | (%, tumor volume ratio of treated group/tumor volume ratio of control) | | | | |
| Control: | — | 3.58 ± 0.25 | 5.31 ± 0.41 | 6.255 ± 0.60 | 8.08 ± 1.29 | 10.61 ± 1.57 |
| HPRI: (ipx6/week, 4 week) | 100 | 2.65 ± 0.19* (74.0) | 2.60 ± 0.11**** (49.0) | 8.30 ± 0.15*** (52.8) | 3.48 ± 0.52** (43.1) | 5.27 ± 0.28* (49.7) |

| Treatment | Dose (ng/mouse) | Tumor weight ratio (volume after treatment/volume ± SE before treatment) | | | | |
|---|---|---|---|---|---|---|
|  |  | 17th day | 21st day | 23rd day | 25th day | 28th day |
|  |  | (%, tumor volume ratio of treated group/tumor volume ratio of control) | | | | |
| Control: | — | 13.43 ± 1.88 | 15.22 ± 3.04 | 17.09 ± 3.50 | 18.63 ± 3.20 | 19.99 ± 3.17 |
| HPRI: (ipx6/week, 4 week) | 100 | 6.56 ± 0.52** (48.9) | 7.81 ± 0.59 (51.3) | 8.45 ± 0.55 (49.5) | 10.39 ± 0.72 (55.7) | 12.39 ± 0.73 (62.0) |

HPRI: Ribonuclease inhibitor
Significant difference of treated groups relative to the control:
*$P < 0.05$.
**$P < 0.02$.
***$P < 0.01$.
****$P < 0.001$

EXAMPLE 8

Antimetastatic Effect of Ribonuclease Inhibitor against Lewis Lung Tumor Cells

Lewis lung tumor cells were intradermally transplanted to the right ears of female BDFI mice (5 week old), and the ribonuclease inhibitor was intraperitoneally administered in a dose of from 10 to 1,000 ng/mouse, continuously for 10 days from 1st day after the transplantation of tumors. The primary nests were surgically delivered on 14th day after the transplantation of tumors. Thereafter, the mice were killed on 21st day, and the metastasis of tumor cells to the lungs and chest lymph nodes was made clear by the measurement of the metastatic weight of lymph nodes and number of lung-metastasized nodes. For comparison, similar experiments were also made on known carcinostatic agents 5-FU, lentinan and cortisone acetate administered in given doses. Results obtained are shown in Table 11.

In the administration of ribonuclease inhibitor in a dose of from 10 to 1,000 ng/mouse, no tumor multiplication suppressive action was seen on 14th day, and 51.7% of lung-metastasis suppression and 56.0% of lymph node-metastasis suppression were seen under an optimum administration condition of 50 ng/mouse/day. On the other hand, 49.5% of lung-metastasis suppressive effect was seen in the administration of 5-FU (5 mg/kg/day, ip×10), but the metastasis to the lungs increased twice in the administration of cortisone acetate (50 mg/kg/day, ip×10). The reason for this increase in the metastasis to the lungs is unclear, but there is also the possibility that the increase depends on the immunosuppresive action induced by cortisone acetate. Also in view of the fact that no lung-metastasis suppressive effect was seen at all in the administration of the lentinan, which is what is called the immunopotentiation agent (1 mg/kg/day ip×10), the action of suppressing the lung and lymph node-metastasis, attributable to the ribonuclease inhibitor, is presumed not to result from the mechanism of only the immunopotentiation action.

TABLE 11

Antimetastatic effect of ribonuclease inhibitor against Lewis lung cancer (LLC)

| Treatment | Dose (ng/mouse) | Weight change, 21st day (g) | Number | Average tumor weight 14th day (mg) ± SE | (treated group/control) (%) | Average metastatic weight of lymph nodes 21st day (mg) ± SE | (treated group/control) (%) | Average number of lung-metastasized nodes 21st day (number) + SE | (treated group/control) (%) |
|---|---|---|---|---|---|---|---|---|---|
| Control: | — | −1.70 | 21 | 767 ± 76 | — | 7.4 ± 0.8 | — | 24.1 ± 3.7 | — |
| Buffer solution: | | +2.00 | 8 | 617 ± 165 | 80.4 | 5.6 ± 1.3 | 78.1 | 20.9 ± 2.0 | 86.7 |
| HPRI: | 1000 | −1.95 | 6 | 548 ± 97 | 71.4 | 7.9 ± 1.0 | 103.7 | 13.8 ± 3.8 | 57.5 |
| | 500 | +0.85 | 6 | 786 ± 207 | 102.4 | 2.8 ± 1.3 | 38.3 | 23.0 ± 10.6 | 95.6 |
| | 100 | −1.47 | 6 | 913 ± 227 | 119.0 | 4.7 ± 2.0 | 63.2 | 13.2 ± 1.2** | 54.9 |
| | 50 | −1.39 | 8 | 481 ± 70* | 62.7 | 3.3 ± 0.8*** | 44.0 | 11.6 ± 2.7** | 48.3 |
| | 10 | +2.22 | 8 | 781 ± 114 | 101.8 | 4.4 ± 1.3 | 59.9 | 17.0 ± 3.8 | 70.7 |
| 5-FU: | 5 mg/Kg | +1.85 | 7 | 534 ± 944 | 69.6 | 3.3 ± 0.8*** | 44.5 | 12.1 ± 3.4* | 50.5 |
| Lentinan: | 1 mg/Kg | +1.80 | 8 | 1098 ± 179 | 143.1 | 6.7 ± 1.8 | 86.3 | 24.0 ± 5.6 | 99.8 |
| Cortisone acetate: | 50 mg/Kg | −0.38 | 8 | 433 ± 106 | 56.5* | 4.3 ± 1.1* | 57.5 | 50.3 ± 8.3*** | 208.9 |

HPRI: Ribonuclease inhibitor
Significant difference of treated groups relative to the control:
*$P < 0.05$.
**$P < 0.02$.
***$P < 0.01$

What is claimed is:

1. A method of controlling lung tumor cell metastasis, comprising administering to a human a therapeutically effective amount of a ribonuclease inhibitor.

2. The method of controlling tumor cell metastasis according to claim 1, wherein said ribonuclease inhibitor is administered to the human body in an amount of 2.5 to 5 μg/kg.

3. The method of controlling tumor cell metastasis according to claim 1, wherein the metastasis is metastasis to the lungs or metastasis to the lymph nodes.

4. The method of controlling tumor cell metastasis according to claim 2, wherein the ribonuclease inhibitor is administered intravenously, subcutaneously, intramuscularly or intratumorously.

5. The method of controlling tumor cell metastasis according to claim 4, wherein the ribonuclease inhibitor is administered in admixture with a sterilized sodium phosphate buffered saline solution containing glutathione.

6. The method of controlling tumor cell metastasis according to claim 1, wherein the metastasis is metastasis to the lungs.

7. The method of controlling tumor cell metastasis according to claim 5, wherein the metastasis is metastasis to the lymph nodes.

* * * * *